United States Patent [19]

Buckl et al.

[11] 4,137,395

[45] Jan. 30, 1979

[54] PROCESS FOR THE TWO-STAGE COMPOSITION OF THE HEMICELLULOSES OF XYLANE-CONTAINING NATURAL PRODUCTS FOR THE PURPOSE OF OBTAINING XYLOSE

[75] Inventors: Hans Buckl, Freising-Tümtenhausen; Rudolf Fahn, Gammelsdorf, both of Germany

[73] Assignee: Süd-Chemie Aktiengesellschaft, Munich, Germany

[21] Appl. No.: 744,210

[22] Filed: Nov. 22, 1976

[30] Foreign Application Priority Data

Nov. 28, 1975 [DE] Fed. Rep. of Germany ....... 2553647

[51] Int. Cl.$^2$ .......................... C07H 1/00; C07H 1/08

[52] U.S. Cl. .................................. 536/1; 260/124 R; 568/852

[58] Field of Search ............ 536/1; 260/124 R, 635 C

[56] References Cited

U.S. PATENT DOCUMENTS

| | | | |
|---|---|---|---|
| 2,174,651 | 10/1939 | Byrkit, Jr. | 260/635 C |
| 2,642,462 | 6/1953 | Kasehagen | 260/635 C |
| 2,650,941 | 9/1953 | Koome et al. | 260/635 C |
| 3,546,296 | 12/1970 | Gobron et al. | 260/635 C |
| 3,586,537 | 6/1971 | Steiner et al. | 260/635 C |
| 3,954,497 | 5/1976 | Friese | 260/635 C |
| 3,970,712 | 7/1976 | Friese | 260/635 C |
| 3,990,904 | 11/1976 | Friese et al. | 260/635 C |

*Primary Examiner*—Johnnie R. Brown

*Attorney, Agent, or Firm*—Sprung, Felfe, Horn, Lynch & Kramer

[57] ABSTRACT

A process for the two-stage decomposition of hemicelluloses of xylane-containing natural products is disclosed for the purpose of obtaining xylose and/or xylitol. According to the process, in a first stage natural products containing xylane are brought into contact with an alkali hydroxide solution and the residue conveyed into a subsequent extraction zone where it is extracted. In a second stage the extraction residue of the first stage is brought into contact with dilute acid and the residue conveyed into a subsequent extraction zone is extracted. The process is characterized in particular that the treated material is moved continuously in both stages in successive reactors by conveyor devices having different conveying performances, e.g., different lengths, cross-sections, speeds of conveying and the like.

15 Claims, 1 Drawing Figure

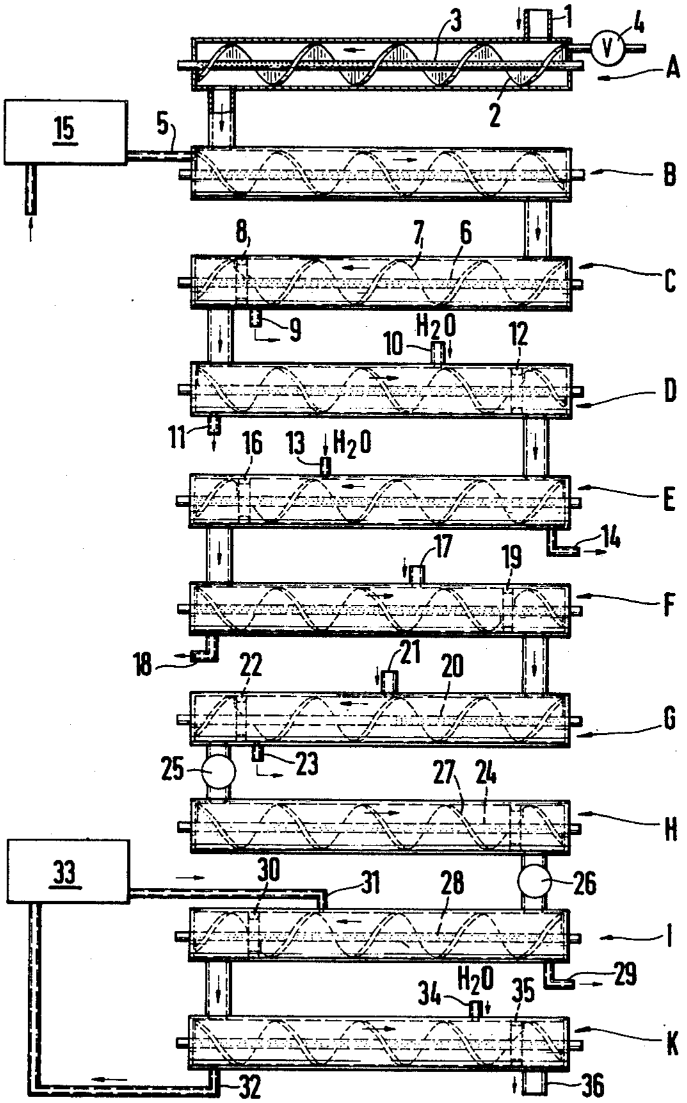
1
4
V
3
A
2
15
5
B
8
7
6
C
9
10
H2O
12
D
11
16
13
H2O
E
14
17
19
F
18
22
21
20
G
25
23
27
24
H
33
30
31
28
26
I
29
34
H2O
35
K
32
36

PROCESS FOR THE TWO-STAGE COMPOSITION OF THE HEMICELLULOSES OF XYLANE-CONTAINING NATURAL PRODUCTS FOR THE PURPOSE OF OBTAINING XYLOSE

BACKGROUND OF THE INVENTION

FIELD OF THE INVENTION

This invention relates to a two-stage process for the decomposition of the hemicelluloses of xylane-containing natural products for the purpose of realizing xylose and/or xylitol. More especially this invention relates to a process for contacting xylane-containing natural products with an alkali metal hydroxide solution, extracting the residue obtained therefrom, feeding the extracted residue to a subsequent stage wherein the same is contacted with an acid and extracting the residue resulting therefrom. This invention is particularly concerned with such a two-stage decomposition performed in a series of reactors containing conveyor devices having different conveying performances.

DISCUSSION OF THE PRIOR ART

D-(+)-xylose and its hydrogenation product, xylitol, have a considerable technical importance. Xylose can be used, for example, in the foodstuffs industry for various purposes, while xylitol has proved a very good sweetening agent for diabetics. Almost solely deciduous wood types, such as beech and chestnut, are used as starting material for the industrial production of xylose. The yields lie at 10–12% (see for example German Pat. Specification No. 912,440).

The obtaining of xylose from oat husks is known from German Pat. Specification No. 834,079. In this process the oat husks are heated to boiling point with 0,08% ammonia or extracted with a benzene-alcohol mixture. Then the usual pressure hydrolysis takes place with 0.2 to 0.5%, $H_2SO_4$ at 125° C. No further processing takes place.

In the pre-treatment with $NH_3$, 4 kg of $NH_3$ are used as 0.08% solution for every 1000 kg of oat husks, in order to split off the acetic acid, however, 17 kg of $NH_3$ are necessary. Moreover, under the conditions stated in the German Patent Specification, it is hardly possible to split off and thus remove the acetic acid, which amounts to about 6% of the weight of the oat husks.

On the basis of this process, in German Publication Specification Nos. 2,358,407 and 2,358,472 of the applicants, processes are proposed for the production of xylose solutions by digestion of deciduous wood or oat husks with a basic agent and treatment of the solid residue obtained with mineral acid. These processes, which are characterized in that alkali hydroxide is used as basic agent, firstly permit the complete exploitation of the starting material and also produce a high xylose yield.

In these processes, when certain xylane-containing natural products were used, especially oat husks, straw and bagasse, great swelling occurred during the alkaline digestion. A short time after the boiling temperature was reached, the volume of the swollen material shrank to about 20%. In the subsequent acid treatment a further great decrease of volume took place, that is to about half of the volume in the swollen condition.

From this it appears that a relatively high reactor volume is necessary for the alkaline decomposition, which volume is no longer required for the subsequent acid decomposition. Therefore, the invention is based upon the problem of carrying out the process so that the available reactor volume is optimally exploited, that is, a smaller reactor volume can be used in the second stage.

It is therefore an object of this invention to provide a process for the two-stage decomposition or digestion of the hemicelluloses of xylane-containing natural products for the purpose of obtaining xylose in which the initial material is treated in the first stage with a basic agent and the obtained residue is subjected to the second stage to an acid treatment.

SUMMARY OF THE INVENTION

Broadly, this invention contemplates an improvement in a process for the two-stage decomposition or digestion of the hemicelluloses of xylane-containing natural products for the purpose of obtaining xylose in which the initial material is first treated in a first stage with a basic agent and the residue obtained therefrom is subjected in a second stage to acid treatment, the improvement residing in that the material for treatment is moved continuously in both stages in successive reactors by conveying devices with different conveying performances while (a) in the first stage the starting material is brought into contact with an alkali hydroxide solution and the residue conveyed into a subsequent extraction zone is extracted, and (b) in the second stage the extraction residue of the first stage is brought into contact with dilute acid and the residue conveyed into a subsequent extraction zone is extracted and wherein the dilute acid solution issuing from stage (b) is worked up to obtain xylose or xylitol and, if desired, the alkali hydroxide solution issuing from the stage (a) is worked up to provide organic acids and lignin.

The different conveying performance, (conveyed volume of treatment material per unit of time) which is necessary in order to compensate for the swelling during the alkali treatment and the subsequent volume shrinkage in the acid treatment, can be achieved in various ways. One can, for example, vary the lengths and cross-sections of the respective reactors and the speeds of the conveyor devices in the respective reactors. Furthermore, if worms are installed as conveyor devices, their pitches can be adapted to the different behavior of the treatment material. In this way the vailable reactors can be optimally exploited, that is, smaller reactors suffice in the second stage.

In the execution of the process in accordance with the invention, the heretofore usual filter presses can be eliminated, as the residue occurring in the first stage does not need to be transferred from the reaction vessel into a filter press and thence after washing into a second reaction vessel and after the acid decomposition again into a filter press.

As xylane-containing natural products there may be considered, for example, wood waste, especially of deciduous wood, such as beech, birch or oak wood; oat husks, grasses, straw, for example, wheat, rye, barley, oat, rice straw, etc; maize cobs, bagasse, reeds, shells of hard-shelled nuts such as coconut shells, almond shells, the shells of palm kernels, olive kernels, date stone, "babacou" nuts and similar hard-shelled nuts. In these products a more or less great reduction of volume occurs in the acid decomposition.

The process according to the invention is especially suitable in the case of xylane-containing natural products which swell strongly in contact with alkaline solution, for example, oat husks, straw (for example, wheat, rye, barley, oat, rice straw, etc.), maize cobs and bagasse.

The alkali treatment in stage (a) is preferably carried out at normal pressure or slightly elevated pressure and the acid treatment in stage (b) is preferably carried out at elevated pressure.

The pressures in stage (a) ordinarily lie between normal pressure and about 3 bar, preferably about 1.5 and 2.5 bar. The temperatures lie between about 80 and 120° C., preferably between about 100 and 110° C. The times of sojourn in stage (a) ordinarily lie at about 15 to 90, preferably about 45 to 75 minutes. Of course, one can also use lower temperatures, in which case longer holding times are necessary in order to split off the bound acetic acid. On the other hand at higher temperatures there is danger of disintegration of the pentosans taking place.

The concentration of the alkali hydroxide solution in stage (a) also influences the decomposition time and the disintegration of the pentosans, for which reason an approximately 0.05 to 0.5 molar alkali hydroxide solution is preferably used. In the case of higher alkali hydroxide concentrations, soluble lignin-xylose complexes, for example, can form which lead to a reduction of the xylose yield.

The alkali content of the alkali hydroxide solution used in stage (a) of the process according to the invention should suffice for the splitting off and neutralization of the bound acetic acid contained in the utilized xylane-containing natural products. This is the case if at least 1 mol of alkali is used per mol of bound acetic acid. Moreover, the crystallization-inhibiting nitrogen-containing substances and other accompanying substances, regarding the nature of which nothing is yet known, pass into solution, while the pentosan is not attacked by the alkali hydroxide in the concentration used. The acetic acid bound to the alkali can be liberated by acidulation and distilled off and, if desired, obtained from the distillate by extraction with a suitable solvent.

One preferably uses 1 to 2 mol, especially 1.1 to 1.2 mol, of alkali hydroxide per mol of bound acetic acid. When alkali hydroxide is used in a quantity of about 2 mol, the destruction of the pentosans and thus a reduction of xylose yield makes itself noticeable. The quantity of bound acetic acid can easily be ascertained by an experimental digestion.

In the extraction following upon the alkali treatment, which extraction is preferably carried out in counter-current, a lower temperature is preferably used than in the alkali treatment, so that the extraction liquid can penetrate better into the pores of the material. The extraction liquid separated from the solid residue and the washing liquid possibly used for the afterwashing can be used for the preparation of the alkali hydroxide solution with which the starting material is treated.

Ordinarily the acid treatment in stage (b) will be carried out at temperatures of about 100 to 150° C., preferably about 120 to 140° C., the acid quantity expediently being so dimensioned that it is just taken up by the solid extraction residue of stage (a). Here either a precisely measured quantity of acid can be introduced into the reaction vessel, or firstly the acid can be supplied in excess and the excess can be pressed off. The limitation of the acid quantity has the advantage that the decomposition takes place in a mild manner, that is only the hemicelluloses are decomposed and the undesired furfurol formation is reduced, so that higher xylose yields are achieved.

The acid treatment is ordinarily carried out with dilute mineral acid, although organic acids such as oxalic acid can also be used. As mineral acids one uses for example $H_2SO_4$, HCl or HBr, but preferably $H_2SO_4$ in a concentration of about 0.5 to 5% by weight, the treatment time amounting in this case to about 15 to 45 minutes.

The extraction after the acid treatment in stage (b) is preferably carried out in counter-current. It is expedient to work at a temperature of about 20 to 130° C., preferably about 50 to 110° C.

Thus the extraction temperature ordinarily is somewhat lower than the treatment temperature, whereby again the penetration of the extraction liquid into the pores of the material is promoted.

It has further proved advantageous to supply steam during the alkali and/or acid treatment, possibly also during the subsequent extractions. The steam serves for the heating or maintenance of temperature in the reaction vessel, whereby especially the extraction rate is increased. It is especially advantageous to supply the steam during the alkali treatment, since in this way the separation of the basic extract and the after-washing of the residue are facilitated.

The supply of steam heats up the starting material or the residue to a temperature of about 100 to 150° C. This measure leads not only to an improved separation or washing-out effect, but in combination with the measure that a liquid colder by about 10 to 60° C. is suddenly added to the pre-heated starting material or residue, to the further advantage that the steam condenses in the pores of the starting material or residue and the colder liquid is sucked into the pores by the occurring vacuum. In this way the exchange of materials is improved.

BRIEF DESCRIPTION OF DRAWING

The process according to the invention is explained in greater detail by reference to the accompanying diagrammatic drawing.

DISCUSSION OF SPECIFIC EMBODIMENT

The raw material (oat husks, straw, bagasse and the like) is introduced at 1 into the reactor A. which is equipped with a conveyor device, for example a worm 2. The length of the reactor or the pitch or rotation speed of the worm 2 are so selected that the conveyed material has a holding time of about 10 minutes. In the reactor A the steaming of the raw material is effected by the introduction of steam through the perforated hollow shaft 3 on which the worm turns are seated. Venting takes place through the valve 4.

After the steaming, the material at about 110° C. is mixed with dilute aqueous NaOH of 60° C. in the reactor B. The liquor (0.5 to 1.0% by weight = 0.125 to 0.25 molar) is added at 5. The concentrated washing liquor coming from the second extraction in the reactor E is expediently used as starting liquid.

Then the solid-liquid mixture is heated in the reactor C with steam through the perforated hollow shaft 6 of the conveyor device 7 to 110° C. The length of the reactor and the pitch or rotation speed of the conveyor device 7 are designed so that a holding time of about 1 hour is reached. The more or less great swelling, dependent upon the respective raw material, occurring firstly in the first third and the subsequent reduction of volume (approximately as from the middle of the reactor) are expediently compensated by a different pitch of the conveyor worm 7 or by a cross-section variation of the reactor C. For this purpose the reactor C can also be divided into two reactors with separate conveyor devices. Additional heating can be effected with the aid of a steam jacket (not shown) of the reactor C. At the end of the reactor C there is a baffle ring 8. A part of the spent liquor flows away at 9.

Now the extraction of the material takes place in the reactor D in counter-current with an extraction liquid which is fed in at 10. For this purpose for example water of 90° C. can be used. The spent liquor is withdrawn at 11. Both this and the spent liquor withdrawn at 9 can be worked up for the obtaining of organic acids (for example acetic acid) and/or lignin. By way of the baffle ring 12 the material is pressed out to about 60% moisture and subjected in the reactor E to a second counter-current extraction, for example with water of 90° C. which is introduced at 15. The washing liquor occurring at 14, containing only a little NaOH, is pumped into the mixing container 15 and re-used after concentration.

The material pressed out again by way of the baffle ring 16 to about 16% moisture is washed in the reactor F in counter-current with dilute acid, for example sulphuric acid at 90° C. which enters at 17, in order to remove the remainder of NaOH from the material. The acid waste water is conducted away at 18.

After the pressing out on the baffle ring 19 to about 60% moisture the material is firstly heated up in the reactor G by means of steam for example to 110° C., the steam being supplied through the perforated shaft 20 in the entry part of the reactor G. In the adjoining part of the reactor, into which no more steam is introduced, the hydrolysis acid is supplied at 21, expediently in a quantity which just suffices for the covering of the material. Dilute sulphuric acid in preferably used with a temperature of about 60° C. The excess acid is pressed off on the baffle ring 22 and leaves the reactor G through the outlet conduit 23. The drained acid is stored up and reintroduced at 21.

Now the acid hydrolysis takes place in the reactor H. The mixture containing about 60% dilute acid is heated with direct steam through the perforated hollow shaft 24 to about 135° C. corresponding to 3.5 bar. A pressure equalisation with the preceding reactor G or with the succeeding reaction I can be prevented, for example, with the aid of the sluice wheels 25,26 or with the aid of appropriate pumps. The length of the reactor H and the conveyor device 27 are so dimensioned that the sojourn time amounts to about 30 min. The repeated volume reduction of 30 to 40%, which occurs towards the reactor end, can be taken into account as in the reactor C by a different pitch of the conveyor worm or by a variation of cross-section or by a division of the reactor H.

After passing through the reactor H the material travels by way of 26 into the reactor I, which is heatable by means of direct steam (through the perforated shaft 28), where it is extracted in counter-current with the dilute solutions (31/32) deriving from the final washing, for example at 90° C. The thin liquor flowing away at 29 is worked up for xylose and possibly for xylitol.

After pressing out through the baffle ring 30 the material is subjected in the reactor K once again to an extraction in counter-current with an extraction liquid (for example water of 90° C.) introduced at 34. The very dilute xylose solution obtained at 32 is re-used for the extraction by way of a reservior 33, possibly after warming to 90° C. The residue pressed out on the baffle ring 25 to about 60% moisture is discharged at 36.

All reactors can be heated either directly with steam through the perforated shaft or through a steam jacket.

The invention is further explained by the following example of execution.

For the alkaline pre-treatment oat husks (about 10% moisture) are heated up in the reactor A with conveyor device by means of steam to about 110° C., whereby a pressure of about 1.5 bar establishes itself. During a time of sojourn of about 10 minutes steaming is effected with the valve 4 slightly opened.

After the steaming the material passes into the reactor B, where it is mixed with aqueous NaOH with a concentration of about 0.5 to 1.0% by weight of NaOH, with a temperature of about 60° C. The inflow of liquor at 5 is so regulated that 300 liters are supplied per 100 kg of material.

In the reactor C then the solid liquid mixture is again heated by steam directly to 110° C. and kept for 1 hour at this temperature. After the mixture has travelled through the reactor in the prescribed time of sojourn, it is extracted in the reactor D in counter-current with water of 90° C. For this purpose 250 liters of water of 90° C. are introduced at 10 per 100 kg of material. The obtained extract is withdrawn and forwarded for further treatment or working up for the obtaining of organic acids (for example acetic acid) and ligmin. The pre-treated material is pressed out by way of the baffle ring 12 to about 60% moisture before it is subjected in the reactor E to a second extraction with water of 90° C. Water requirement about 300 liters per 100 kg of material. The departing weak spent liquor is re-used as starting liquor in the reactor B after/enrichment with NaOH.

Now a washing also follows with 100 liters/100 kg of a 0.05% by weight sulphuric acid of 90° C. in the reactor F in counter-current. The temperatures in the extractions and in the $H_2SO_4$ washing can be maintained by steam supply.

The residue remaining after the alkali pre-treatment, after pressing out to about 60% moisture (baffle ring 19) is first heated up in the reactor G with steam to 110° C. and then mixed, approximately as from the middle of the reactor, with 2.5% sulphuric acid of 60° C. The excess acid (now about 1.5%) withdrawn at 23 is added again as 21 after concentration. The mixture is pressed out through the baffle ring 22 to about 100% moisture and heated in the reactor 8 with direct steam and possible jacket heating to 135° C. corresponding to 3.5 bar. The conveyor device of the reactor is designed so that a time of sojourn of 30 min. is achieved. After hydrolysis has been effected the material is extracted in the reactor I with dilute hydrolysis solution of 90° C. from the second extraction (reactor K). The 200 liters of hydrolysis solution obtained per 100 kg of material have a concentration of about 15% xylose. The total yield of xylose in the extract (in relation to raw material) amounts to 80%.

The first extraction is also followed by a second with water of 90° C. in the reactor K. The very dilute extraction solution occurring here is re-used for the first extraction. The water requirement amounts to 200 liters per 100 kg of residue.

What is claimed is:

1. In a process for the two-stage decomposition of the hemicelluloses of xylane-containing natural products for the purpose of obtaining xylose solutions, wherein the starting material is treated with an alkali hydroxide solution in the first stage and the obtained residue is subjected in the second stage to a dilute acid treatment, the improvement wherein the treated material is moved continuously in both stages in successive reactors by conveyor devices with different conveying performances, while (a) in the first stage the starting material is brought into contact with an alkali hydroxide solution and the residue conveyed into a subsequent extraction zone is extracted with an extraction liquid, and (b) in a second stage the extraction residue of the first stage is brought into contact with dilute acid and the residue conveyed into a subsequent extraction zone is extracted with another extraction liquid and wherein in at least one of the alkali or the acid treatment, the starting material or the residue is pre-heated with steam to a temperature of about 100° to 150° C. and suddenly the alkali hydroxide solution, or the dilute acid, or one of the extraction liquids colder by about 10° to 60° C. is added.

2. A process according to claim 1 wherein the extraction in at least one of stages (a) or (b) is carried out in counter-current.

3. A process according to claim 1 wherein the alkali treatment in stage (a) is carried out at pressures of from atmospheric pressure to 3 bar and the acid treatment in stage (b) is carried out at pressures corresponding to temperatures of from 100 to 150° C.

4. A process according to claim 1 wherein in stage (a) an approximate 0.05 to 0.5 molar alkali hydroxide solution is used.

5. A process according to claim 1 wherein the dilute acid treatment in stage (b) is carried out with the acid quantity being dimensioned so that it is just taken up by the solid extraction residue of stage (a).

6. A process according to claim 1 characterized in that the dilute acid treatment in stage (b) is carried out with dilute mineral acid.

7. A process according to claim 1 wherein the extraction after the dilute acid treatment in stage (b) is carried out at a temperature about 20 to 130° C.

8. A process according to claim 5 wherein the dilute acid treatment of stage (b) is carried out at a temperature of 120–140° C.

9. A process according to claim 6 wherein the mineral acid is 0.5 to 5 weight percent sulfuric acid solution.

10. A process according to claim 5 wherein the dilute acid treatment is performed for a period of time of about 15 to 45 minutes.

11. A process according to claim 1 wherein steam is supplied to the mass during the subsequent extraction zone following treatment of the starting material with the alkali hydroxide solution.

12. A process according to claim 1 wherein steam is supplied to the subsequent extraction zone following contacting the extraction residue of the first stage with dilute acid.

13. A process according to claim 7 wherein the acid treatment is effected at a temperature of 50 to 110° C.

14. A process for the two-stage decomposition of the hemicellulose of a xylane-containing natural product to produce a xylose solution which consists essentially of:

(a) in a first stage contacting the natural product with an alkali metal hydroxide solution while moving the natural material continuously by a conveyor device and extracting the residue from the alkali metal hydroxide treatment with an extraction liquid, and (b) in a second stage contacting the residue from the first stage with dilute acid while moving the same continuously in a successive reactor by a conveying device having a different conveying performance than the conveyor device used in the first stage and extracting the residue from the acid extraction with another extraction liquid and removing liquid effluent from the first stage and the second stage and wherein in at least one of the alkali or acid treatments the starting material or the residue is pre-heated with steam to a temperature of about 100° to 150° C. and suddenly the alkali metal hydroxide or dilute acid or one of the extraction liquids which is colder by 10° to 60° C. is added thereto.

15. A process according to claim 1 wherein the acid is mineral acid or oxalic acid.

* * * * *

UNITED STATES PATENT AND TRADEMARK OFFICE

CERTIFICATE OF CORRECTION

PATENT NO. : 4,137,395

DATED : January 30, 1979

INVENTOR(S) : BUCKL et al.

It is certified that error appears in the above-identified patent and that said Letters Patent are hereby corrected as shown below:

Title Page, Title, [54], "COMPOSITION" should read -- DECOMPOSITION --.

Column 1, line 1, "COMPOSITION" should read -- DECOMPOSITION --.

Column 6, line 2, "reservior" should read -- reservoir --.

Column 6, line 50, "as" should read -- at --.

Signed and Sealed this

*Twenty-ninth* Day of *May 1979*

[SEAL]

*Attest:*

RUTH C. MASON
*Attesting Officer*

DONALD W. BANNER
*Commissioner of Patents and Trademarks*